United States Patent
Ueda et al.

(10) Patent No.: US 7,608,636 B2
(45) Date of Patent: *Oct. 27, 2009

(54) MEDICINES FOR TREATMENT AND PREVENTION OF NEUROGENIC PAIN

(75) Inventors: Hiroshi Ueda, Nagasaki (JP); Munehiro Tomikawa, Chiba (JP)

(73) Assignee: Hamilton Pharmaceuticals, Inc., Washington, DC (US)

( * ) Notice: Subject to any disclaimer, the term of this patent is extended or adjusted under 35 U.S.C. 154(b) by 668 days.

This patent is subject to a terminal disclaimer.

(21) Appl. No.: 10/450,524

(22) PCT Filed: Dec. 25, 2001

(86) PCT No.: PCT/JP01/11356

§ 371 (c)(1),
(2), (4) Date: Oct. 20, 2003

(87) PCT Pub. No.: WO02/053153

PCT Pub. Date: Jul. 11, 2002

(65) Prior Publication Data

US 2004/0063776 A1 Apr. 1, 2004

(30) Foreign Application Priority Data

Dec. 28, 2000 (JP) ............................... 2000-400679

(51) Int. Cl.
*A61K 31/40* (2006.01)
(52) U.S. Cl. ..................................... 514/424; 514/816
(58) Field of Classification Search ................. 514/424, 514/343, 423, 816
See application file for complete search history.

(56) References Cited

U.S. PATENT DOCUMENTS 3,459,738 A 8/1969 Morren (Continued)

FOREIGN PATENT DOCUMENTS

CA 1288347 * 9/1991

(Continued)

OTHER PUBLICATIONS

Ubels et al. "Walking training for intermittent Claudication in diabetes," Diabetes care, 1999, vol. 22, No. 2, pp. 198-201.*

(Continued)

*Primary Examiner*—Shengjun Wang
(74) *Attorney, Agent, or Firm*—Howrey LLP

(57) ABSTRACT

A medicament for therapeutic and/or prophylactic treatment of neuropathic pain, which comprises a compound represented by the general formula (I) or a pharmaceutically acceptable salt thereof as an active ingredient:

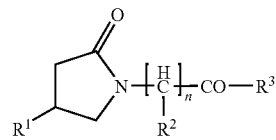

wherein $R^1$ represents a hydrogen atom or a hydroxyl group; $R^2$ represents a hydrogen atom or an alkyl group having 1 to 3 carbon atoms; $R^3$ represents a phenyl group which may have 1 to 3 atoms or substituents selected from the group consisting of a halogen atom, a hydroxyl group, an alkyl group having 1 to 3 carbon atoms, and an alkoxyl group having 1 to 3 carbon atoms, or represents —NH—$R^4$ wherein $R^4$ represents a phenyl group which may have 1 to 3 atoms or substituents selected from the group consisting of a halogen atom, a hydroxyl group, an alkyl group having 1 to 3 carbon atoms, and an alkoxyl group having 1 to 3 carbon atoms or hydrogen atom, and n represents 0 or 1.

5 Claims, 5 Drawing Sheets

U.S. PATENT DOCUMENTS

| | | | |
|---|---|---|---|
| 4,118,396 | A | 10/1978 | Pifferi et al. |
| 4,341,790 | A | 7/1982 | Betzing et al. |
| 4,369,139 | A | 1/1983 | Kyburz et al. |
| 4,431,641 | A | 2/1984 | Mondadori et al. |
| 4,620,973 | A * | 11/1986 | Truog .......................... 514/34 |
| 4,696,943 | A | 9/1987 | Gobert et al. |
| 4,837,223 | A | 6/1989 | Gobert et al. |
| 4,943,639 | A | 7/1990 | Gobert et al. |
| 5,232,700 | A * | 8/1993 | Centifanto .................. 424/400 |
| 5,551,846 | A | 9/1996 | Taylor et al. |
| 5,885,976 | A * | 3/1999 | Sandyk ........................ 514/159 |
| 5,886,023 | A | 3/1999 | Otomo et al. |
| 5,919,803 | A * | 7/1999 | Giblin et al. ................. 514/329 |
| 6,107,330 | A | 8/2000 | Nabeshima et al. |
| 6,281,242 | B1 | 8/2001 | Regan et al. |
| 6,365,621 | B1 | 4/2002 | Tanaka et al. |
| 6,399,650 | B2 * | 6/2002 | Otomo et al. ................ 514/424 |
| 6,417,220 | B2 | 7/2002 | Yoshii et al. |
| 6,423,739 | B1 * | 7/2002 | Otomo et al. ................ 514/424 |
| 2004/0077709 | A1 * | 4/2004 | Murashima et al. ......... 514/424 |

FOREIGN PATENT DOCUMENTS

| | | | |
|---|---|---|---|
| EP | 0 243 336 | A | 10/1987 |
| EP | 0408524 | | 1/1991 |
| EP | 1 020 189 | A | 7/2000 |
| JP | 42-19093 | | 9/1967 |
| JP | 52-23072 | | 2/1977 |
| JP | 54-117468 | | 9/1979 |
| JP | 56-2960 | | 1/1981 |
| JP | 60-252461 | | 12/1985 |
| JP | 61-280470 | | 12/1986 |
| JP | 62-5404 | | 2/1987 |
| JP | 3-048657 | | 3/1991 |
| JP | 3-46466 | | 7/1991 |
| JP | 4-160496 | | 6/1992 |
| JP | 04219093 | A2 | 8/1992 |
| JP | 5-163144 | | 6/1993 |
| JP | 5-163145 | | 6/1993 |
| JP | 6-65197 | | 3/1994 |
| WO | WO 97/06319 | * | 2/1997 |
| WO | 98/14213 | | 4/1998 |
| WO | WO 98/14213 | | 4/1998 |
| WO | 00/07593 | | 2/2000 |
| WO | WO 00/07593 | | 2/2000 |
| WO | 00/72844 | | 12/2000 |
| WO | WO 00/72844 | A1 | 12/2000 |
| WO | WO 00/78244 | * | 12/2000 |
| WO | WO 01/39779 | A | 6/2001 |

OTHER PUBLICATIONS

Gouliaev et al. "Piracetam and other structurally related nootropics," Brain Research Review, 1994, vol. 19, pp. 180-222.*

Hitzenberger et al. "Pharmacological properties of piracetam, rational for use in stroke patients," CNS Drug; 1998, vol. 9, suppl 1, pp. 19-27.*

Glas-Schottl "Piracetam in the treatment of soft tissue rheumatism," Fortschritte der Medizin, 1989, vol. 107, No. 13, pp. 298-302.*

The Merck Manual, fifteenth edition, pp. 1380-1387.*

"Carpal tunnel syndrome" Wikipedia, http://en.wikipedia.org/wiki/Carpal_tunnel_syndrome.*

Danilova et al. "The effect of piracetam and its combination with sodium hydroxybutyrate in neuropathic pain syndrom," Eksperimental' naya i Klinicheskaya Farmakologiya (1996), vol. 59, No. 4, pp. 8-10, CAPLUs Abstract.*

Gwak et al. "Activation of spinal GABA receptors attenuates chronic ventral neuropathic pain after spinal cord injury," Journal of Neurotrauma, 2006, vol. 23, pp. 1111-1124.*

Rashid et al. "Nonopioid and neuropathy-specific analgesic action of the nootropic drug nefiractem in mice," The Journal of Pharmacology and experimental therapeutics, 2002, vol. 303, No. 1, pp. 226-231.*

English Language Abstracts JP3-48657.

Hirato, M., Igaku no Ayumi, vol. 195, No. 9, 2000, 12.2, pp. 627-632, 2000.

Ye, X. et al., "Botulinum Toxin C3 Inhibits Hyperalgesia in Mice with Partial Sciatic Nerve Injury," *Jpn. J. Pharmacol.*, vol. 83, pp. 161-163.

Malmberg, A.B., "Partial Sciatic Nerve Injury in the Mouse as a Model of Neuropathic Pain: Behavioral and Neuroanatomical Correlates," *Pain*, vol. 76, pp. 215-222, 1998.

Database Medline 'Online! US National Library of Medicine (NLM), Bethesda, MD, US ; Jul. 1996, Danilova E I et al.: "The action of piracetam and its complex with sodium oxybutyrate in the neuropathic pain syndrome!"; XP002361863; Database accession No. NLM9026199 & Eksperimental 'Naia I Klinicheskaia Farmakologiia. Jul.-Aug. 1996, vol. 59, No. 4, Jul. 1996, pp. 8-10, ISSN: 0869-2092.

Kitano Y et al.: "General Pharmacological Profile of the New Cognition-Enhancing Agent Nefiracetam Allgemeines Pharmakologisches Profil Des Neuen Nootropikums Nefiracetam" Arzneimittel Forschung. Drug Research, ECV Editio Cantor Verlag, Aulendorf, DE, vol. 44, No. 2A, Feb. 1994, pp. 199-210, XP001073794, ISSN: 0004-4172.

Chong M S et al.: "Anticonvulsants for the Management of Pain" Pain Reviews, Arnold, London, GB, vol. 7, No. 3/4, 2000, pp. 129-149, XP008016567, ISSN: 0968-1302, p. 139, right-hand column, paragraph 2.

Nabeshima T: "Ameliorating Effects of Nefiracetam (DM-9384) on Brain Dysfunction" Drugs of Today / Medicamentos De Actualidad, J.R. Prous SS.A. International Publishers, ES, vol. 30, No. 5, Jul. 1994, pp. 357-379, XO001034923, ISSN: 0025-7656.

Ardid D et al.: "Levetiracetam (keppra), a new antiepileptic drug, is effective in neuropathic but not acute pain models in rats", Neurology, vol. 56, No. 8 Supplement 3, Apr. 24, 2001(Nov. 1, 2001), pp. A350-A351, XP008057865 & 53$^{rd}$ Annual Meeting of the American Academy of Neurology; Philadelphia, PA, USA; May 5-11, 2001, issn: 0028-3878.

Aiken S.P. et al.: "Treatment of epilepsy: existing therapies and future developments" Frontiers in Bioscience, No. 5, Nov. 1, 2000, pp. E124-E152, XP002361861, p. 127 paragraph 2.5,6 and p. 137 paragraph 4.2.8.

Kongetsu no Chiryo (Treatment of this Month), vol. 8, No. 3, 2000, Separate Issue, pp. 56-61.

Rashid et al., "Nonopoid and Neuropathy-Specific Analgesic Action of the Nootropic Drug Nefiracetam in Mice," The Journal of Pharmacology and Experimental Therapeutics, vol. 303(1), 226-31 (2002).

* cited by examiner

Von Frey test (n=6 in each group)

MEDICINES FOR TREATMENT AND PREVENTION OF NEUROGENIC PAIN

FIELD OF THE INVENTION

The present invention relates to a medicament for therapeutic and/or prophylactic treatment of neuropathic pain and relates to a supplemental analgesic agent.

BACKGROUND ART

Pains in terminal cancer patients are serious problems, and it is an important object to release cancer patients from their pains to improve quality of life of the patients. Conventionally, narcotic analgesics, morphine as a typical example, have been used for pain treatments of such cancer patients. It is known that, among the types of pains in cancer, there is intractable neuropathic pain (the pain is called as "neuropathic pain" or "neurogenic pain", and will be referred to as "neuropathic pain" in the specification) for which morphine is hardly effective, besides somatic pain caused by noxious stimulus in peripheries such as mechanical stimulus, chemical stimulus and thermal stimulus, and visceral pain caused by stimulus such as dilatation of membranes due to traction or enlargement of parenchymal organs and elevation of internal pressure of hollow organs.

Normally, pains are generated by damages of tissues at the corresponding tissue portions, and the pains will be dispersed when the tissue damages are cured. However, although no tissue damage is observed at the site of the pain, pains may sometimes be generated such as burning, constricting, pricking or electrification-like pain. Such pains are called neuropathic pains, and the pains are caused by damages or dysfunctions of peripheral or central nerves.

Although the neuropathic pain may be independently generated, it is considered that, in cancer pain, the pain is combined and mixed with somatic pains in about 30% of cases. In drug therapy of neuropathic cancer pain, antidepressants, anticonvulsants, local anesthesia, $\alpha_2$ agonists, GABA receptor agonists, NMDA receptor antagonists and so forth have been used as supplemental analgesic agents for narcotic analgesics and the like. However, they, per se, have severe side effects, and moreover, they may sometimes deteriorate the side effects of morphine which is administered to most of cancer patients, since they have low compatibility with morphine. Therefore, a supplemental analgesic agent has been desired which has high safety and good congeniality with morphine (Kongetsu no Chiryo (Treatment of This Month), Vol.8, No. 3, 2000, Separate Issue).

Furthermore, it is known that neuropathic pains are observed not only in cancer pains but in postherpetic neuralgia, post-thoracotomic pain, diabetic neuropathy, CRPS (complex regional pain syndrome, those in which nervous damages are not apparently observed are referred to as "type-1" (reflux sympathetic dystrophy (RSD) and those in which nervous damages are observed are referred to "type-2" (causalgia)), multiple sclerosis, AIDS, trigeminal neuralgia, thalamic pain, paraplegic pain caused by myelopathy, anesthesia dolorosa, or phantom limb pain (Igaku no Ayumi (Advance of Medicine), Vol. 195, No.9, 2000.12.2, pp.627-632).

DISCLOSURE OF THE INVENTION

An object of the present invention is to provide a compound effective for neuropathic pain.

Another object of the present invention is to provide a medicament for therapeutic and/or prophylactic treatment of neuropathic pain.

Still another object of the present invention is to provide a supplementary agent for therapeutic and/or prophylactic treatment of neuropathic pain.

The inventors of the present invention conducted various studies to achieve the foregoing objects. As a result, they found that the compound represented by the general formula (I) and pharmaceutically acceptable salts thereof had excellent suppressing effects on neuropathic pain. The present invention was achieved on the basis of the above finding.

The present invention thus provides a medicament for therapeutic and/or prophylactic treatment of neuropathic pain which comprises as an active ingredient a compound represented by the general formula (I) or a pharmaceutically acceptable salt thereof:

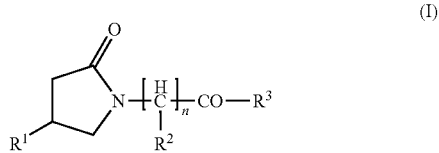

(I)

wherein $R^1$ represents a hydrogen atom or a hydroxyl group,
$R^2$ represents a hydrogen atom or an alkyl group having 1 to 3 carbon atoms,
$R^3$ represents a phenyl group which may have 1 to 3 atoms or substituents selected from the group consisting of a halogen atom, a hydroxyl group, an alkyl group having 1 to 3 carbon atoms, and an alkoxyl group having 1 to 3 carbon atoms, or represents —NH—$R^4$ ($R^4$ represents a phenyl group which may have 1 to 3 atoms or substituents selected from the group consisting of a halogen atom, a hydroxyl group, an alkyl group having 1 to 3 carbon atoms, and an alkoxyl group having 1 to 3 carbon atoms or a hydrogen atom), and
n represents 0 or 1.

The present invention also provides a medicament for suppressing neuropathic pain which comprises the compound represented by the aforementioned general formula (I) or a pharmaceutically acceptable salt thereof as an active ingredient; and a medicament as supplemental analgesic treatment which comprises the compound represented by the aforementioned general formula (I) or a pharmaceutically acceptable salt thereof as an active ingredient (hereinafter in the specification, the medicament is occasionally referred to as a "supplemental analgesic agent").

According to the aforementioned inventions, examples of the neuropathic pain include, for example, cancer pains, postherpetic neuralgia, post-thoracotomic pain, diabetic neuropathy, CRPS, multiple sclerosis, AIDS, trigeminal neuralgia, thalamic pain, paraplegic pain caused by myelopathy, anesthesia dolorosa, phantom limb pain and the like.

In the aforementioned medicaments, the compound represented by the general formula (I) may preferably be 2-oxo-1-pyrrolidineacetamide (piracetam), 4-hydroxy-2-oxo-1-pyrrolidineacetamide (oxiracetam), 1-(4-methoxybenzoyl)-2-pyrrolidinone (aniracetam), (S)-α-ethyl-2-oxo-1-pyrrolidineacetamide (levetiracetam), or N-(2,6-dimethylphenyl)-2-(2-oxo-1-pyrrolidinyl)acetamide (nefiracetam), and among them, 4-hydroxy-2-oxo-1-pyrrolidineacetamide or N-(2,6-dimethylphenyl)-2-(2-oxo-1-pyrrolidinyl)acetamide is more preferred, and N-(2,6-dimethylphenyl)-2-(2-oxo-1-pyrrolidinyl)acetamide is most preferred.

From further aspect, provided are a method for therapeutic and/or prophylactic treatment of neuropathic pain which comprises the step of administering to a mammal including human a therapeutically and/or prophylactically effective amount of the compound represented by the above general formula (I) or a salt thereof; a method for suppressing neuropathic pain which comprises the step of administering to a mammal including human an effective amount of the compound represented by the above general formula (I) or a salt thereof; a method for supplemental treatment of therapeutic and/or prophylactic treatment of neuropathic pain which comprises the step of administering to a mammal including human an effective amount of the compound represented by the above general formula (I) or a salt thereof; and a method for therapeutic and/or prophylactic treatment of neuropathic pain which comprises the step of administering to a mammal including human a therapeutically and/or prophylactically effective amount of the compound represented by the above general formula (I) or a salt thereof together with at least one analgesic agent. Further provided is a use of the compound represented by the above general formula (I) or a salt thereof for the manufacture of the aforementioned medicaments.

BEST MODE FOR CARRYING OUT THE INVENTION

Figure 1:
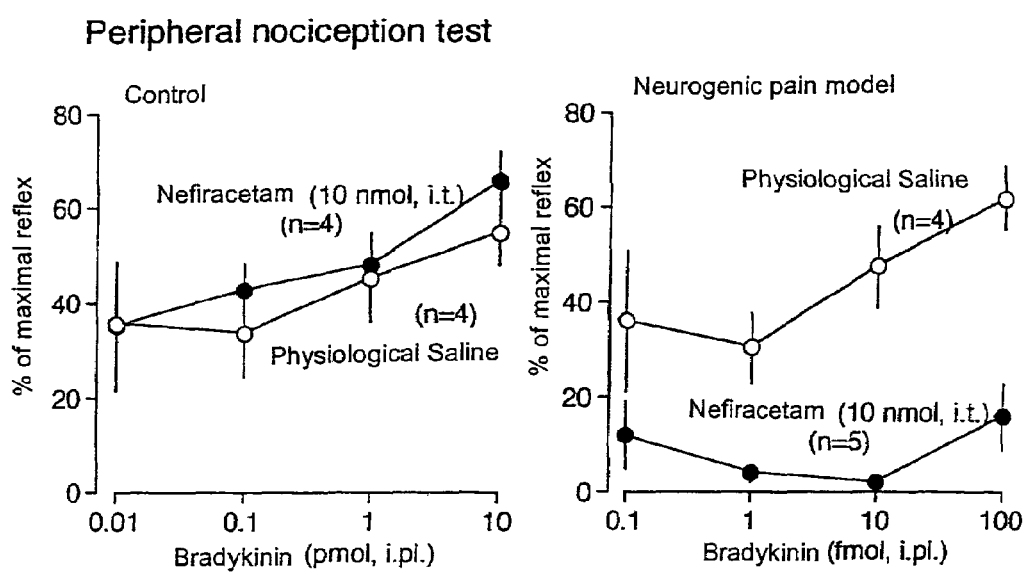
FIG. 1 is a graph showing suppressing effect on neuropathic pain observed in the peripheral nociception test.
Figure 2:
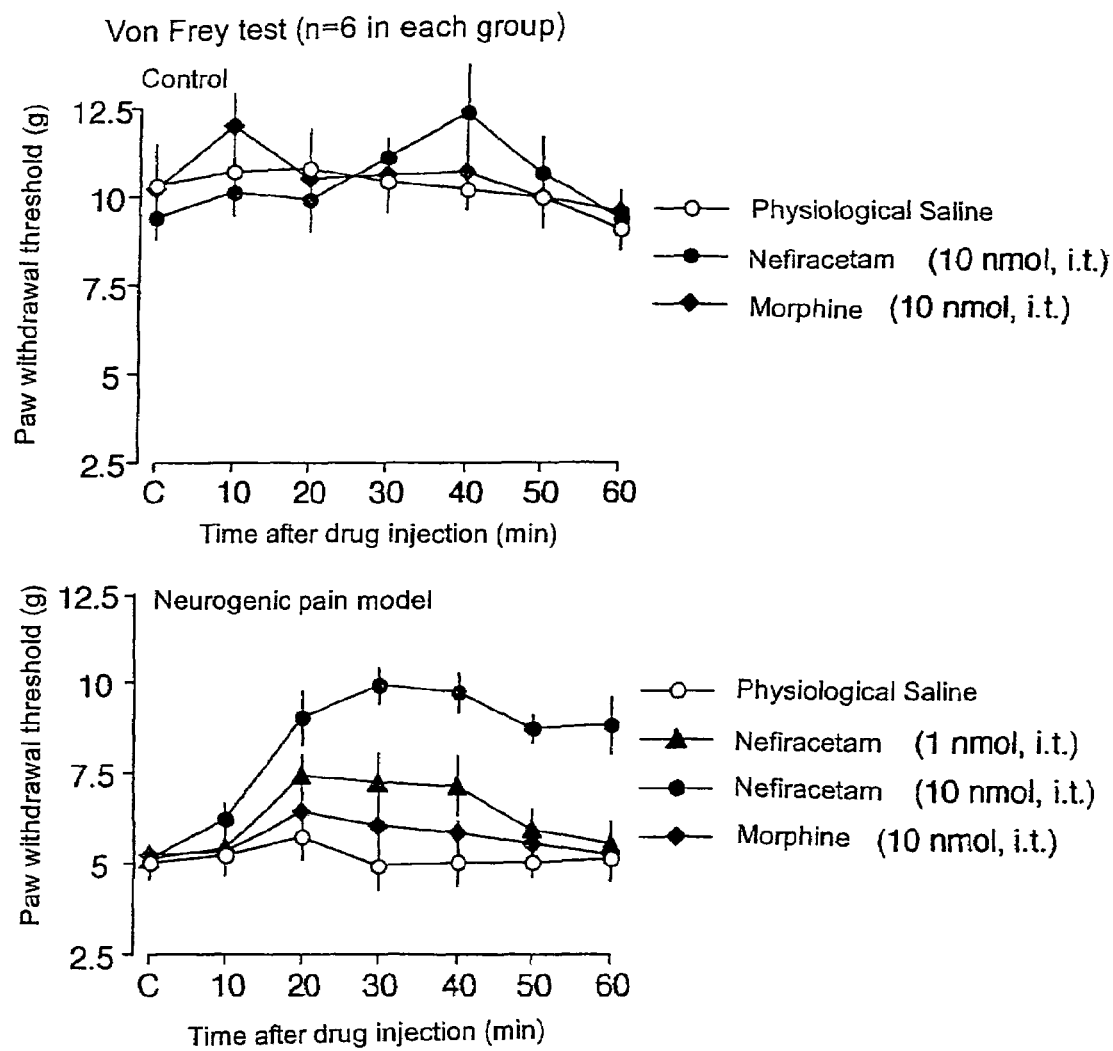
FIG. 2 is a graph showing suppressing effect on neuropathic pain observed in the von Frey test.
Figure 3:
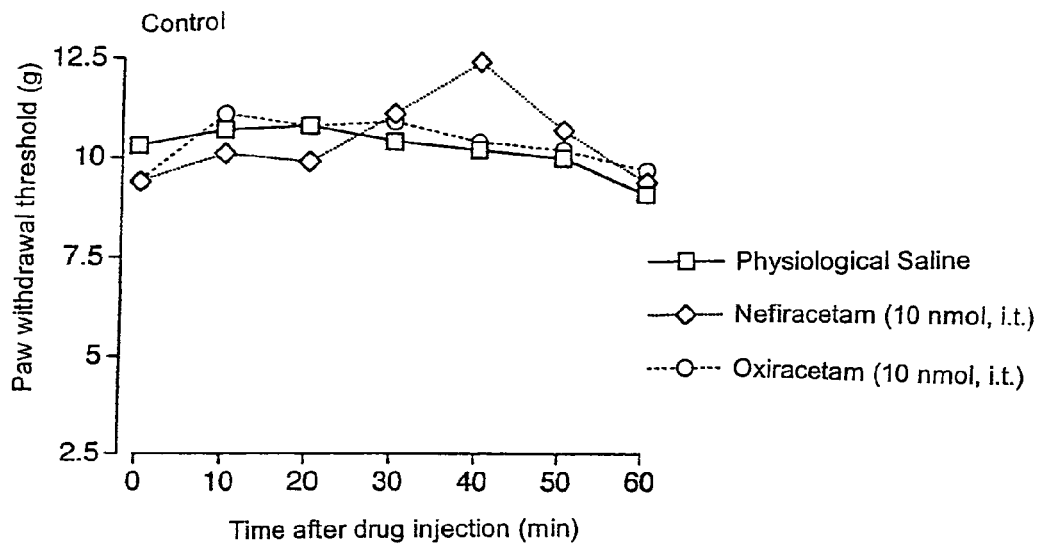
FIG. 3 is a graph showing suppressing effect of oxiracetam on neuropathic pain observed in the von Frey test.
Figure 3:
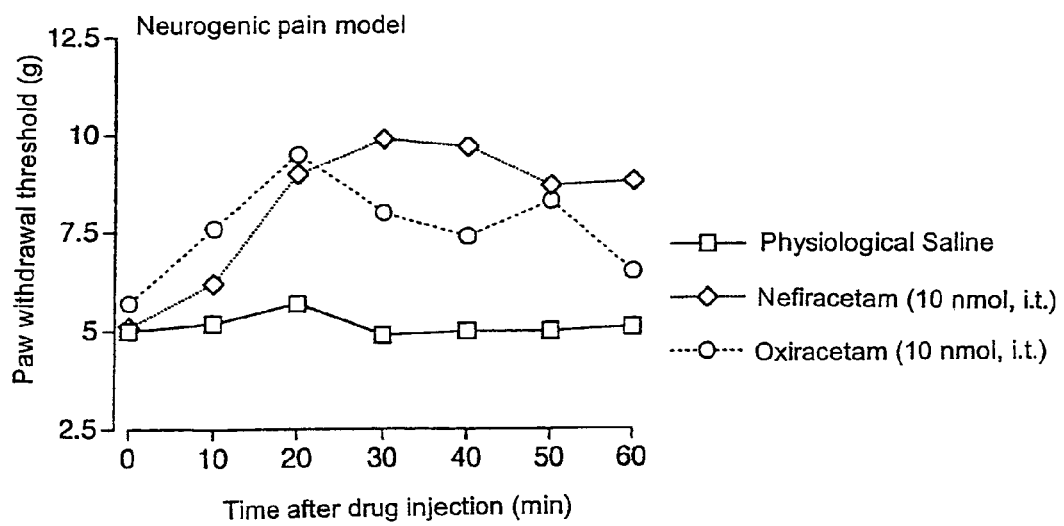
Figure 4:
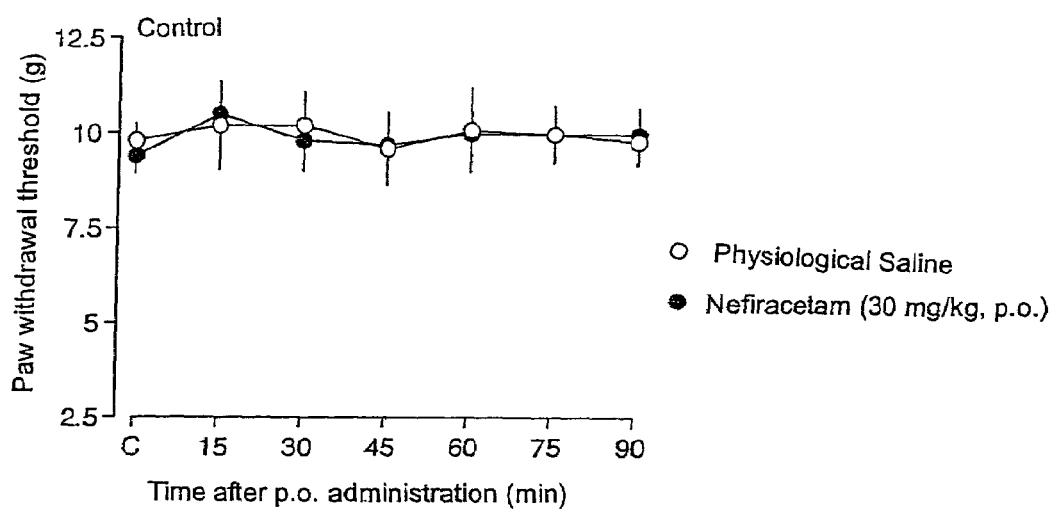
FIG. 4 is a graph showing suppressing effect of nefiracetam on neuropathic pain by oral administration observed in the von Frey test.
Figure 4:
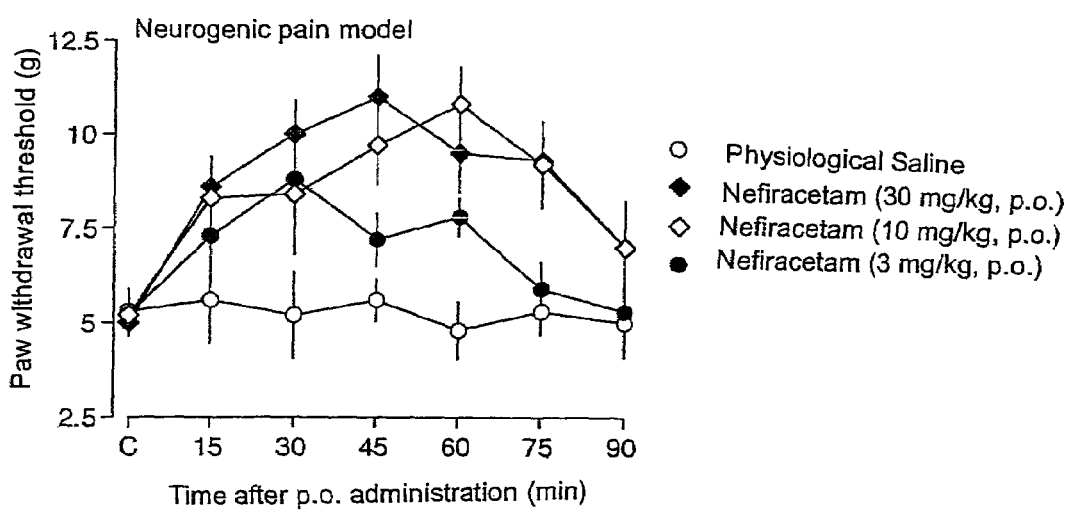
Figure 5:
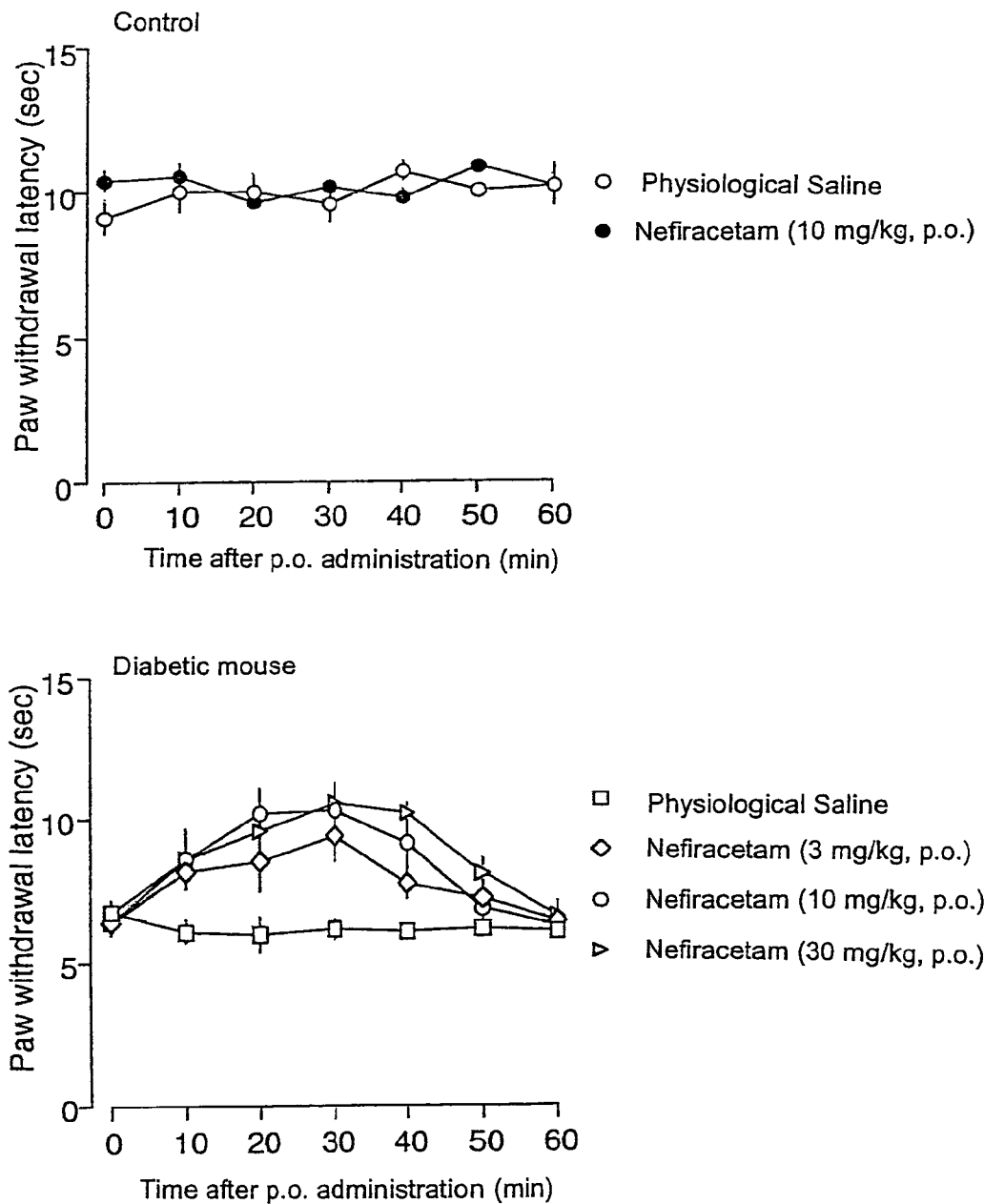
FIG. 5 is a graph showing suppressing effect on diabetic neuropathic pain observed in the Hargreaves test.

The compounds represented by the aforementioned general formula (I) are known compounds disclosed in, for example, Japanese Patent Publication (Kokoku) No. 42-19093, Japanese Patent Unexamined Publication (Kokai) Nos. 52-23072, 54-117468, 60-252461, 56-2960, 61-280470, 4-160496, Japanese Patent Publication No. 3-46466 and so forth. Known pharmacological effects thereof include an effect of improving cerebral functions (Japanese Patent Publication No. 62-5404), an effect of improving Alzheimer type senile dementia (Japanese Patent Unexamined Publication No. 5-163144), an effect of improving cerebrovascular dementia (Japanese Patent Unexamined Publication No. 5-163145), an effect of suppressing generation of dependency and resistance by a narcotic analgesics (U.S. Pat. No. 6,107,330), effect of improving intractable epilepsy (WO00/7593), an effect of stabilizing mitochondria membrane (WO98/14213), an effect of inhibiting neurocyte death (WO00/72844) and so forth. However, the pain suppression effect or supplemental analgesic effect of these compounds has not been known.

These compounds can be easily produced by the methods disclosed in, for example, Japanese Patent Publication No. 42-19093, Japanese Patent Unexamined Publication Nos. 52-23072, 54-117468, 60-252461, 56-2960, 61-280470, 4-160496, Japanese Patent Publication No. 3-46466 and so forth.

In the general formula (I), $R^3$ is preferably a phenyl group having an alkoxyl group or —NH—$R^4$. $R^4$ is preferably a phenyl group having two alkyl groups or hydrogen atom.

Examples of typical compounds among the compounds falling within the scope of the general formula (I) include 2-oxo-1-pyrrolidineacetamide (piracetam), 4-hydroxy-2-oxo-1-pyrrolidineacetamide (oxiracetam), 1-(4-methoxybenzoyl)-2-pyrrolidinone (aniracetam), (S)-α-ethyl-2-oxo-1-pyrrolidineacetamide (levetiracetam), and N-(2,6-dimethylphenyl)-2-(2-oxo-1-pyrrolidinyl)acetamide (nefiracetam). Among them, nefiracetam and oxiracetam are preferred, and nefiracetam is particularly preferred.

As the compounds represented by the general formula (I), compounds either in a free form or in a form of a pharmaceutically acceptable salt may be used. Further, hydrates thereof or solvates thereof can also be used. Examples of the pharmaceutically acceptable salts include, for example, mineral acid salts such as hydrochlorides, hydrobromides, hydroiodides, sulfates, nitrates, and phosphates, and organic acid salts such as acetates, maleates, fumarates, citrates, oxalates, succinates, tartrates, malates, mandelates, methanesulfonates, p-toluenesulfonates and 10-camphorsulfonates.

The compounds represented by the general formula (I) and pharmaceutically acceptable salts thereof have analgesic effect on neuropathic pain in experimental models of neuropathic pain as shown in the examples. Therefore, the compounds represented by the general formula (I) and pharmaceutically acceptable salts thereof are useful as medicaments for therapeutic and/or prophylactic treatment of neuropathic pain such as cancer pain, postherpetic neuralgia, post-thoracotomic pain, diabetic neuropathy, CRPS, multiple sclerosis, AIDS, trigeminal neuralgia, thalamic pain, paraplegic pain caused by myelopathy, anesthesia dolorosa, phantom limb pain and the like. Furthermore, they are also useful as supplemental analgesic agents for medicaments used for treatment of pain, for example, narcotic analgesics used for treatment of cancer pain and the like.

Routes of administration of the medicament of the present invention are not particularly limited, and the medicament can be orally or parenterally administered. The compounds represented by general formula (I) or pharmaceutically acceptable salts thereof, per se, as the active ingredients may be used as the medicament of the present invention. Generally, the medicament may be provided as pharmaceutical preparations well known to those skilled in the art by adding pharmaceutically acceptable additives.

Examples of pharmaceutical preparations suitable for oral administration include, for example, tablets, capsules, powders, subtilized granules, granules, solutions, syrups and the like, and examples of pharmaceutical preparations suitable for parenteral administration include, for example, injections for subcutaneous, intravenous or intramuscular injections, drip infusions, suppositories, inhalants, transdermal preparations, transmucosal preparations, patches and the like.

As the pharmaceutically acceptable additives, for example, excipients, disintegrating agents or disintegrating aids, binders, lubricants, coating agents, coloring matters, diluents, bases, dissolving agents or dissolving aids, isotonic agents, pH modifiers, stabilizers, propellants, adherents and the like may be used.

Doses of the medicament of the present invention is not particularly limited, and can be suitably selected depending on the route of administration, degree of neuropathic pain, therapeutic or prophylactic purpose, the age, symptoms and body weight of a patient and the like. For example, the dose for oral administration may be about 20 to 2000 mg, preferably about 30 to 900 mg per day as the weight of the compound represented by the general formula (I) or the pharmaceutically acceptable salt thereof, and the aforementioned daily dose may be administered as several divided portions. Acute toxicity of nefiracetam, which is a typical example of the compounds represented by the general formula (I), is 2,005 mg/kg (male mouse, p.o.), and therefore the compounds are highly safe (Japanese Patent Unexamined Patent Publication No. 5-163144).

Further, the medicaments of the present invention can generally be used as supplemental analgesic agents concurrent with narcotic analgesic agents which themselves are provided in a form of a solution, a tablet or the like. Methods for the combined use are not particularly limited. Examples of employable methods include a method in which the medicament of the present invention is continuously administered during the same and whole period as the administration period of a narcotic analgesic; a method in which the medicament of the present invention is occasionally administered as required during the administration period of a narcotic analgesic; a method in which administration of the medicament of the present invention is started before administration of a narcotic analgesic, and then administrations of the narcotic analgesic and the medicament of the present invention are continued; a method in which a narcotic analgesic and the medicament of the present invention are continuously administered, then the administration of the narcotic analgesic is stopped and the administration of the medicament of the present invention is further continued and the like. If required, a pharmaceutical composition comprising a narcotic analgesic and the active ingredient of the medicament of the present invention (so-called a combined drug) may be prepared and administered.

EXAMPLES

The present invention will be more specifically explained with reference to the following examples. However, the scope of the present invention is not limited to the following examples.

Example 1

Suppressing Effect on Neuropathic Pain in Peripheral Nociception Test 17 of ddY male mice having a body weight of 13 to 15 g were used. The mice were anesthetized with pentobarbital, and skin of right hind leg of each mouse was dissected so that sciatic nerve was observed. The half of sciatic nerve fibers was bound with a suture for 9 mice among 17 mice, and only the dissection was performed for the remaining 8 animals (a control group). After the dissection site was sutured, the animals were left for 7 days (Xun Ye et al, Jpn. J. Pharmacol. 2000, Malmberg A B and Basbaum A I, Pain 1998). The mice had a body weight of 20 to 22 g after being left. The group of mice of which sciatic nerves were bound was divided into two groups, and mice of one group were each administered with 5 µl (10 nmol) of nefiracetam and mice of the other group were each administered with 5 µl of physiological saline into spinal subarachnoid space. After the administration, the mice were each subcutaneously administered at a right hind leg footpad with physiological saline at 10 minutes and 15 minutes, 2 µl (0.1 fmol) of bradykinin at 20 minutes and 25 minutes, 2 µl (1 fmol) of bradykinin at 30 minutes and 35 minutes, 2 µl (10 fmol) of bradykinin at 40 minutes and 45 minutes, and 2 µl (100 fmol) of bradykinin at 50 minutes and 55 minutes after the administration. The group of mice that were subjected only to the dissection was also divided into two groups, and mice of one group were each administered with 5 µl (10 nmol) of nefiracetam and mice of the other group were each administered with 5 µl of physiological saline into spinal subarachnoid space. After the administration, the mice were each subcutaneously administered at a right hind leg footpad with physiological saline at 10 minutes and 15 minutes, 2 µl (0.01 pmol) of bradykinin at 20 minutes and 25 minutes, 2 µl (0.1 pmol) of bradykinin at 30 minutes and 35 minutes, 2 µl (1 pmol) of bradykinin at 40 minutes and 45 minutes, and 2 µl (10 pmol) of bradykinin at 50 minutes and 55 minutes after the administration. The noxious flexion reactions caused by the administrations of bradykinin were indicated as a ratio based on the maximum spontaneous flexion reaction.

Example 2

Suppressing Effect on Neuropathic Pain in von Frey Test 42 of ddY male mice having a body weight of 16 to 18 g were used. In the von Frey test, the mice were placed on a mesh, and footpads of the mice were stimulated with a von Frey filament (TRANSDUCER INDICATOR MODEL 1601 (IITC INC., U.S.A.)) every 10 minutes, and the threshold values observed at the beginning of an escape reaction were represented in a unit of gram. The mice were anesthetized with pentobarbital, and skin of right hind leg of each mouse was dissected so that sciatic nerve was observed. The half of sciatic nerve fibers was bound with a suture for 24 mice among 42 mice, and only the dissection was performed for the remaining 18 mice (a control group). After the dissection site was sutured, the animals were left for 7 days (Xun Ye et al, Jpn. J. Pharmacol. 2000, Malmberg A B and Basbaum A I, Pain 1998). The mice had a body weight of 23 to 25 g after being left. The group of mice of which sciatic nerves were bound was divided into 4 groups, and the threshold was measured twice. The average of the values was used as a control value. Then, mice of each group were each administered with 5 µl (1 nmol) of nefiracetam, 5 µl (10 nmol) of nefiracetam, 5 µl (10 nmol) of morphine or 5 µl of physiological saline into spinal subarachnoid space. After the administration, the threshold was repeatedly measured for 60 minutes with intervals of 10 minutes. The group of mice that were subjected only to the dissection was divided into three groups, and a control value was measured in the same manner as described above. Then, mice of each group were each administered with 5 µl (10 nmol) of nefiracetam, 5 µl (10 nmol) of morphine or 5 µl of physiological saline into spinal subarachnoid space, and the threshold was measured in the same manner as described above.

Example 3

Suppressing Effect on Neuropathic Pain in von Frey Test

In the same manner as in Example 2, 5 µl (10 nmol) of oxiracetam was administered and the threshold was measured.

Example 4

Suppressing Effect on Neuropathic Pain by Oral Administration of Nefiracetam in von Frey Test 36 of ddY male mice having a body weight of 16 to 18 g were used. In the von Frey test, the mice were placed on a mesh, and hind leg footpads of the mice were stimulated with a von Frey filament (digital type von Frey tester MODEL 1601 (IITC INC., U.S.A.)) every 15 minutes, and the threshold values observed at the beginning of an escape reaction were represented in a unit of gram. The mice were anesthetized with pentobarbital, and skin of right hind leg of each mouse was dissected so that sciatic nerve was observed. The half of sciatic nerve fibers was bound with a suture for 24 animals among the 36 animals, and only the dissection was performed for the remaining 12 animals (a sham group). After the dissection site was sutured, experiments were performed on the 7th day (Xun Ye et al, Jpn. J. Pharmacol. 2000, Malmberg A B and Basbaum A I, Pain 1998). The mice had a body weight of 23 to 25 g after the 7 days. The group of mice of which sciatic nerves were bound was divided into 4 groups, and the threshold was measured twice. The average of the values was used as a control value. Then, mice of each group were each orally administered with 3 mg/kg, 10 mg/kg or 30 mg/kg of nefiracetam or physiological saline (10 ml/kg), and the threshold was repeatedly measured for 90 minutes with intervals of 15 minutes. The mice of the control group (the sham group) that were subjected only to the dissection were divided into two groups, and a control value was measured in the same manner as described above. Then, mice of each group were each orally administered with 30 mg/kg of nefiracetam or physiological saline (10 ml/kg), and the threshold was measured in the same manner as described above.

Example 5

Analgesic Effect on Diabetic Neuropathic Pain in Hargreaves Test 36 of ddY male mice having a body weight of 28 to 30 g were used. In the Hargreaves test, the mice were placed on a glass plate, and hind leg footpads of the mice were stimulated with radiant heat (combination type analgesia meter MODEL 336 (IITC INC., U.S.A.)) every 10 minutes. And the latent time until the beginning of an escape reaction was measured. The mice with diabetes mellitus were prepared by administering streptozotocin (200 mg/kg) dissolved in 0.1 N citrate buffer (pH 4.5) to caudal arteries, and the experiment was performed on the 7th day. The mice having a blood glucose level of 300 mg/dl or higher under a starved condition (after starvation for 3 hours) were used as mice with diabetes mellitus. 24 animals among the 36 animals were determined as mice with diabetes mellitus according to the method described above, and the remaining 12 mice were administered with 0.1 N citrate buffer at caudal arteries and used as a comparative control group (control group). The mice with diabetes mellitus were divided into 4 groups, and the threshold was measured twice. The average of the values was used as a control value. Then, mice of each group were each orally administered with 3 mg/kg, 10 mg/kg or 30 mg/kg of nefiracetam or physiological saline (10 ml/kg), and the latent time was repeatedly measured for 60 minutes with intervals of 10 minutes. The control group was divided into two groups, and a control value was measured as described above. Then, mice of each group were each orally administered with 10 mg/kg of nefiracetam or physiological saline (10 ml/kg), and the latent time was measured in the same manner as described above.

In the mouse peripheral nociception test, nociceptive flexion reactions caused by chemical pain stimulus using bradykinin were evaluated. In the control group subjected only to the dissection and without nervous disturbance, the effect of nefiracetam, administered into the spinal subarachnoid space at a dose of 0.01 to 10 pmols, on the reaction caused by bradykinin administered to footpad was found to be not significant as compared to that obtained by physiological saline. Whilst in the neuropathic pain model in which the nervous disturbance was generated, an equivalent bradykinin response was caused with a dose in the range of 0.1 to 100 fmol, which was lower by 100 times. The administration of nefiracetam into the spinal subarachnoid space gave strong analgesic effects to an extent that the bradykinin sensitive response was completely suppressed.

In the von Frey test, the escape reactions caused by mechanical noxious stimulus, which was given for a time period of 60 minutes with intervals of 10 minutes, were evaluated as a threshold (g). In the control group subjected only to the dissection and without nervous disturbance, both of the administrations of nefiracetam and morphine into the spinal subarachnoid spaces did not give significant effect as compared to the administration of physiological saline. Whilst in the neuropathic pain model in which the nervous disturbance was generated, the noxious response threshold fell down to an about half level compared with the control group, which indicated sensitivity reaction. The administration of morphine into the spinal subarachnoid space (10 nmol) gave no significant effect on the reaction. However, nefiracetam gave analgesic effect in a dose-dependent manner at doses of 1 and 10 nmol, which were lower than that of morphine, and its degree reached the threshold observed in the control.

Further, oxiracetam gave analgesic effect substantially equivalent to that of nefiracetam in the von Frey test. Nefiracetam also gave suppressing effect on neuropathic pain even by oral administration, and nefiracetam also gave suppression effect also on diabetic neuropathic pain.

As described above, it was demonstrated that the compounds of the present invention represented by the general formula (I) and salts thereof have superior analgesic effects on morphine-resistant neuropathic pain.

INDUSTRIAL APPLICABILITY

The compounds of the present invention represented by the general formula (I) and salts thereof have superior analgesic effects on morphine-resistant neuropathic pain, and therefore, are useful as medicament for therapeutic and/or prophylactic treatment of cancer pain and the like, or as supplemental analgesic agents.

What is claimed is:

1. A method for treating neuropathic pain, consisting essentially of administering to a mammal suffering from neuropathic pain a therapeutically effective amount of nefiracetam, or a pharmaceutically acceptable salt thereof, wherein the neuropathic pain is neuropathic pain of cancer pain, post-thoracotomic pain, diabetic neuropathy, CRPS, multiple sclerosis, AIDS, trigeminal neuralgia, paraplegic pain caused by myelopathy, anesthesia dolorosa, or phantom limb pain.

2. The method according to claim 1, wherein said mammal is a human.

3. The method according to claim 1, wherein said neuropathic pain is neuropathic pain of cancer pain.

4. The method according to claim 1, wherein the neuropathic pain is neuropathic pain of diabetic neuropathy.

5. The method according to claim 1, wherein the neuropathic pain is neuropathic pain of AIDS.

* * * * *

UNITED STATES PATENT AND TRADEMARK OFFICE
CERTIFICATE OF CORRECTION

PATENT NO. : 7,608,636 B2
APPLICATION NO. : 10/450524
DATED : October 27, 2009
INVENTOR(S) : Ueda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 873 days.

Signed and Sealed this

Twelfth Day of October, 2010

David J. Kappos
*Director of the United States Patent and Trademark Office*